United States Patent
Kelley

(10) Patent No.: US 6,966,500 B1
(45) Date of Patent: Nov. 22, 2005

(54) REMOTE CONTROLLED SCENT DISPENSING DEVICE

(76) Inventor: Richard D. Kelley, 29606 Cunningham, Warren, MI (US) 48092

( * ) Notice: Subject to any disclaimer, the term of this patent is extended or adjusted under 35 U.S.C. 154(b) by 0 days.

(21) Appl. No.: 10/822,256

(22) Filed: Apr. 12, 2004

(51) Int. Cl.$^7$ ............................................. A24F 25/00
(52) U.S. Cl. ........................... 239/60; 239/34; 239/47; 239/57; 239/58; 239/71; 43/1
(58) Field of Search .............................. 239/34, 47, 57, 239/58, 145, 67, 69, 71, 60; 43/1

(56) References Cited

U.S. PATENT DOCUMENTS

| | | | |
|---|---|---|---|
| D268,695 S * | 4/1983 | Kolf ........................... D22/125 |
| 4,523,717 A * | 6/1985 | Schwab ........................ 239/56 |
| 4,953,763 A | 9/1990 | Kierum et al. |
| 5,305,541 A | 4/1994 | Simpson |
| 5,611,165 A * | 3/1997 | Blaha .............................. 43/1 |
| 5,746,019 A * | 5/1998 | Fisher ............................. 43/1 |
| D414,931 S * | 10/1999 | Palmer ..................... D3/271.8 |
| 6,241,161 B1 * | 6/2001 | Corbett ......................... 239/58 |
| 6,443,434 B1 | 9/2002 | Prather |
| 6,502,762 B2 * | 1/2003 | Tuttobene, Jr. .............. 239/59 |
| 2003/0020185 A1 | 1/2003 | Cox |

* cited by examiner

Primary Examiner—David A. Scherbel

(57) ABSTRACT

A remote controlled scent dispensing device includes a housing that has a first wall, a second wall and a peripheral wall that extends between and is attached to the first and second walls. The peripheral wall has a peripheral break therein such that the housing is divided into a first portion and a second portion. A moving assembly is mounted in the housing and is adapted for selectively moving the first portion abutting against or positioned away from the second portion. An actuator apparatus is adapted for remotely turning on the moving assembly and selectively moving the first portion with respect to the second portion. A coupler is attached to the housing for selectively coupling the housing to a tree limb. A scent dispensing member is positioned within the housing at a juncture of the first and second portions.

8 Claims, 4 Drawing Sheets

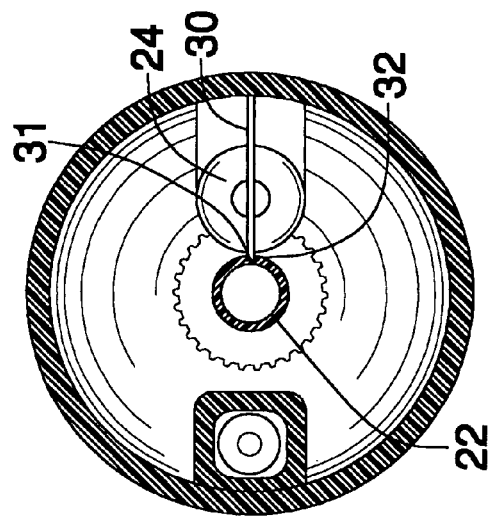
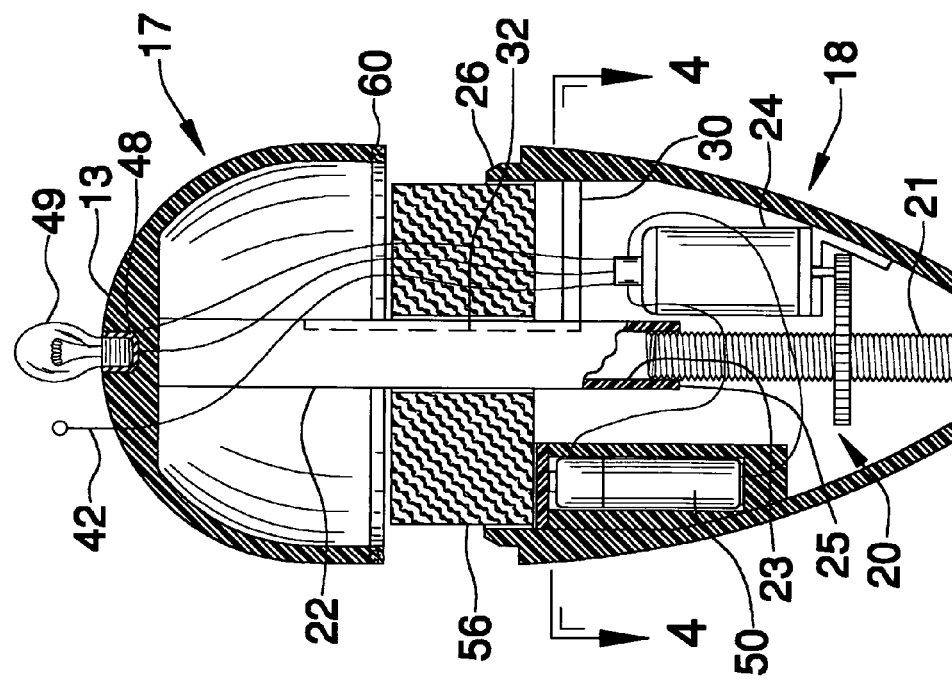

REMOTE CONTROLLED SCENT DISPENSING DEVICE

BACKGROUND OF THE INVENTION

1. Field of the Invention

The present invention relates to scent dispersal devices and more particularly pertains to a new scent dispersal device for selectively dispensing doe scent.

2. Description of the Prior Art

The use of scent dispersal devices is known in the prior art. U.S. Pat. No. 6,502,762 describes a device that may be programmed for selectively emitting a scent stored within. Another type of scent dispersal device is U.S. Pat. No. 4,953,763 that releases scent on a timed basis. U.S. application Ser. No. 2003/0020185 describes a scent dispenser that includes a fan for better dispersal of a scent.

While these devices fulfill their respective, particular objectives and requirements, the need remains for a device that may be actuated remotely to disperse an animal scent, and in particular, doe scent. By being able to remotely control the dispensing device, the user of the device may mount it once within a tree and open it from a remote location only when the hunter is actively hunting. The hunter may use this technique over several days to train male deer to train the male deer to come during certain times to the area being hunted.

SUMMARY OF THE INVENTION

The present invention meets the needs presented above by generally including a housing that has a first wall, a second wall and a peripheral wall that extends between and is attached to the first and second walls. The peripheral wall has a peripheral break therein such that the housing is divided into a first portion and a second portion. A moving assembly is mounted in the housing and is adapted for selectively moving the first portion abutting against or positioned away from the second portion. An actuator apparatus is adapted for remotely turning on the moving assembly and selectively moving the first portion with respect to the second portion. A coupler is attached to the housing for selectively coupling the housing to a tree limb. A scent dispensing member is positioned within the housing at a juncture of the first and second portions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended thereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross-sectional view taken along line 3—3 of FIG. 2 of the present invention.

FIG. 4 is a cross-sectional view taken along line 4—4 of FIG. 3 of the present invention.

DESCRIPTION OF THE PREFERRED EMBODIMENT

Figure 1:
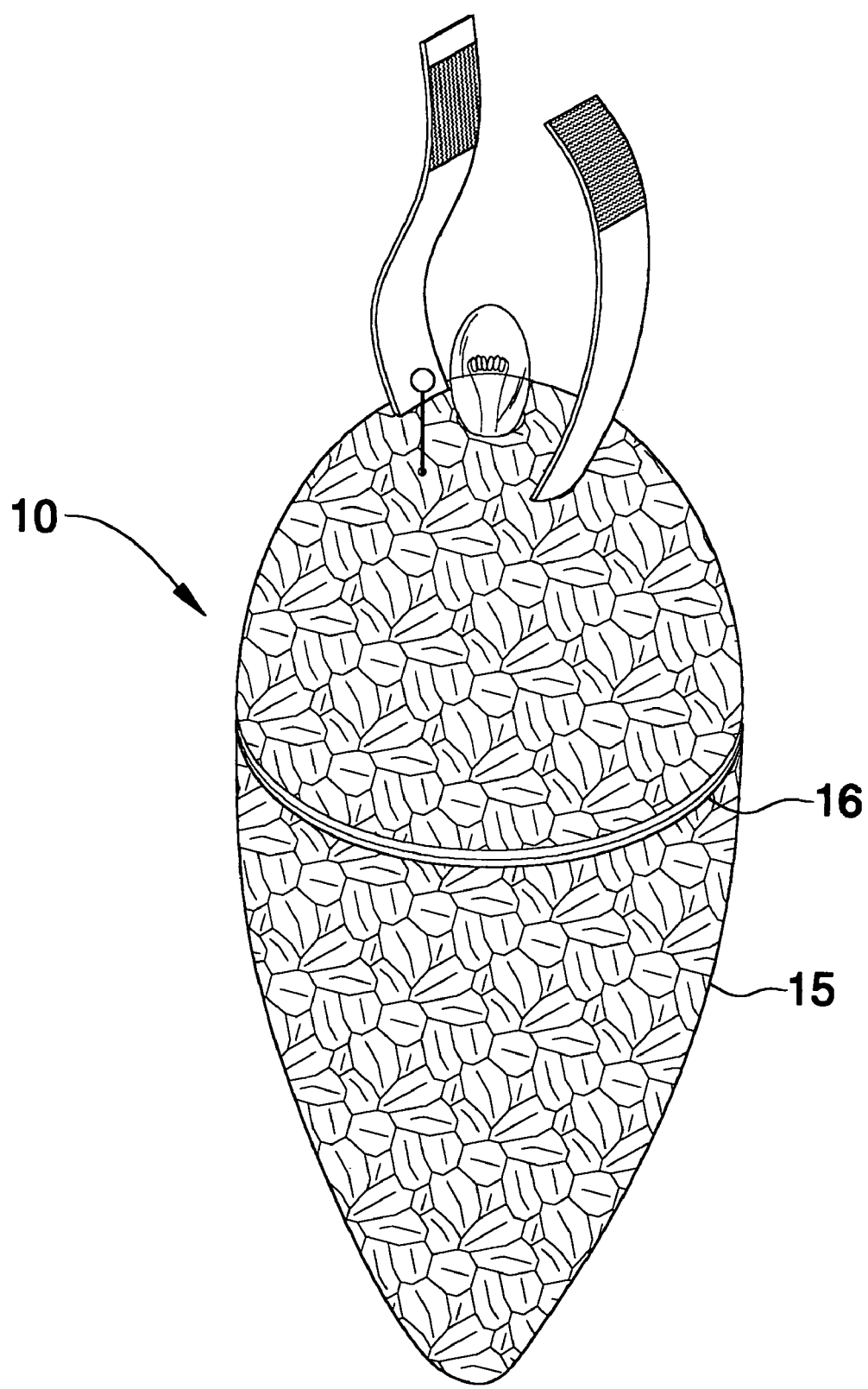
FIG. 1 is a perspective view of a remote controlled scent dispensing device according to the present invention.
Figure 2:
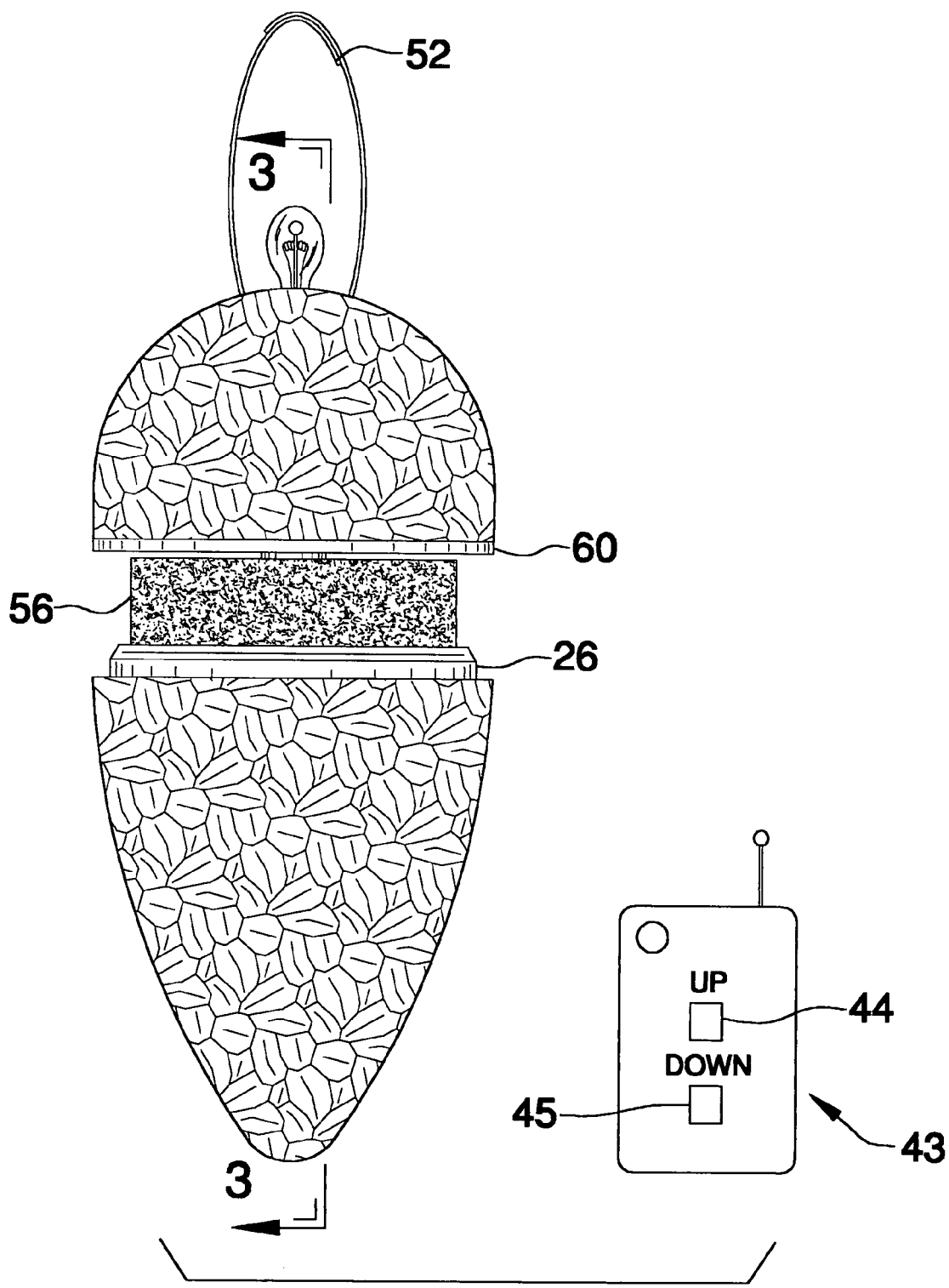
FIG. 2 is a side view of the present invention.
Figure 5:
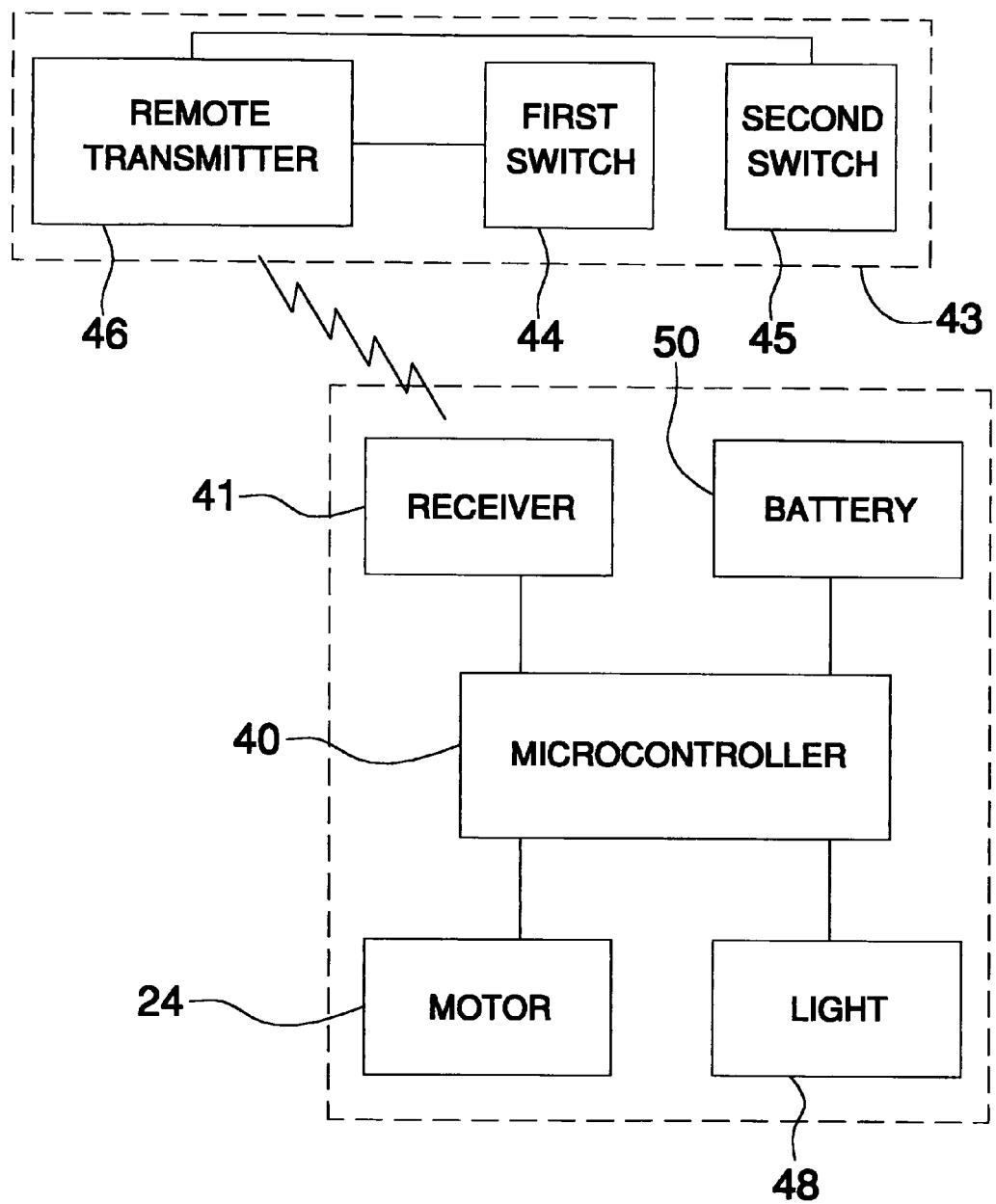
FIG. 5 is an electronic schematic view of the present invention.

With reference now to the drawings, and in particular to FIGS. 1 through 5 thereof, a new scent dispersal device embodying the principles and concepts of the present invention and generally designated by the reference numeral 10 will be described.

As best illustrated in FIGS. 1 through 5, the remote controlled scent dispensing device 10 generally comprises a housing 12 having a first wall 13, a second wall 14 and a peripheral wall 15 that extends between and is attached to the first 13 and second 14 walls. The peripheral wall 15 has a peripheral break 16 therein such that the housing 12 is divided into a first portion 17 and a second portion 18.

A moving assembly 20 is mounted in the housing 12 and is adapted for selectively moving the first portion 17 abutting against or positioned away from the second portion 18. The moving assembly 20 includes a combination of a threaded rod 21 and a tube 22 that has an inner threaded surface 23. The threaded rod 21 extends into and is threadably coupled to the tube 22. The combination is attached to and extends between the first 17 and second 18 portions. A motor 24 is mounted in the housing 12 and is mechanically coupled to the combination. The motor 24 is adapted for selectively causing the rotation of the rod 21 in a first direction with respect to the tube 22 so that the first portion 17 moves away from the second portion 18 and rotation of the rod 21 in a second direction with respect to the tube 22 so that the first portion 17 moves toward the second portion 18.

Preferably, the threaded rod 21 is rotatably coupled to and extends upwardly from the second wall 14. The tube 22 is attached to and extends downwardly from the first wall 13. The rod 21 extends inwardly of an open bottom end 25 of the tube 22 and is threadably coupled to the tube 22. The motor 24 is mechanically coupled to the rod 21 and is adapted for selectively rotating the rod 21 in the first direction or the second direction. When the first 17 and second 18 portions have moved fully toward each other, the first 17 and second 18 portions are joined and a flange 26 attached to the second portion 18 engages the first portion 17.

A support member is mounted in the housing 12 and adapted for preventing rotation of the first portion 17 with respect to the second portion 18. The support member may include any number of methods for preventing the rotation of the first 17 and second 18 portions with respect to each other. FIG. 3 shows an arm 30 for a support member that is mounted in the second portion 18. The arm 30 has a free end 31 extending into an elongated slot 32. The elongated slot 32 is positioned in an outer surface of the tube 22 and generally extends from the first wall 13 toward the bottom end 25. Alternatively, a telescoping pole may be attached to and extended between the first 17 and second 18 portions. The support member also aids in preventing the first 17 and second 18 portions from moving too far away from each other.

An actuator apparatus is adapted for remotely turning on the moving assembly 20 and selectively moving the first portion 17 with respect to the second portion 18. The actuator apparatus includes a control 40 that is mounted in the second portion 18 and is electrically coupled to the motor 24. The control 40 may include a conventional micro controller or microprocessor. A receiver 41 for receiving a wireless signal is electrically coupled to the control 40. An antenna 42 may be mounted on the housing 12 and electrically coupled to the receiver 41. A transmitter 46 is adapted for sending a wireless signal to the receiver 41. A switch assembly 43 is electrically coupled to the transmitter 42. The switch assembly 43 includes at least two switches 44, 45. Depressing a first 44 of the switches causes a first signal to be sent to the control 40 such that the first portion 17 is moved away from the second portion 18. Depressing a second 45 of the switches causes a second signal to be sent to the control 40 such that the first portion 17 moves toward the second portion 18.

A light socket 48 is mounted in the first wall 13. A light bulb 49 is removably positioned in the light socket 48 such that the light bulb 49 extends away from the housing 12. The light socket 48 is electrically coupled to the moving assembly 20 such that the light bulb 49 is turned on when the actuating apparatus 43 actuates the moving assembly 20. A power supply 50 is electrically coupled to the control 40. The power supply 50 is preferably a battery removably mounted in the housing 12.

A coupler 52 is attached to the housing 12 for selectively coupling the housing 12 to a tree limb. The coupler 52 may include a hook, ties, or a pair of straps which may be removably attached together with hook and loop securing means so that the straps can be formed into a loop.

A scent dispensing member 56 is positioned within the housing 12 at a juncture of the first 17 and second 18 portions. The scent dispending member 56 preferably includes an absorbent material that may be selectively removed from the housing 12. A liquid scent may be positioned on and absorbed by the absorbent material so that the scent is dispensed when the housing 56 is opened.

In use, a hunter would typically saturate the absorbent material with doe pheromone scent and then place the absorbent material in the housing 12. The housing 12 is attached to a tree limb, within a decided proximity of the hunting position of the hunter. The hunter uses the actuator apparatus 43 to selectively open and close the housing 12 at the desired times to train the bucks when to be in the area of the device 10. A sealing ring 60 may be attached to and extended along an edge of the first portion 17 to ensure that the scent does not escape except when required by the hunter. It is preferred that the housing 12 is camouflaged as a pine cone and the light 49 aids the hunter in finding the housing 12 after it has been placed in a tree.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A remote control scent dispensing device, said device comprising:

a housing having a first wall, a second wall and a peripheral wall extending between and being attached to said first and second walls, said peripheral wall having a peripheral break therein such that said housing is divided into a first portion and a second portion;

a moving assembly being mounted in said housing and being adapted for selectively moving said first portion abutting against or positioned away from said second portion, said moving assembly including;

a combination of a threaded rod and a tube having an inner threaded surface, said threaded rod extending into and being threadably coupled to said tube, said combination being attached to and extending between said first and second portions;

a motor being mounted in said housing and being mechanically coupled to said combination, said motor being adapted for selectively causing a rotation of said rod in a first direction or a second direction with respect to said tube, wherein the rotation of said rod in a first direction with respect to said tube moves said first portion away from said second portion and rotation of said rod in a second direction with respect to said tube moves said first portion toward said second portion;

an actuator apparatus being adapted for remotely turning on said moving assembly and selectively moving said first portion with respect to said second portion, said actuator apparatus comprising;

a control being mounted in said housing and being electrically coupled to said motor;

a receiver for receiving a wireless signal being electrically coupled to said control;

a transmitter for sending a wireless signal; and a switch assembly being electrically coupled to said transmitter, said switch assembly including at least two switches, wherein depressing a first of said switches causes a first signal to be sent to said control such that said first portion moves away from said second portion, and wherein depressing a second of said switches causes a second signal to be sent to said control such that said first portion moves toward said second portion;

a coupler being attached to said housing for selectively coupling said housing to a tree limb; and a scent dispensing member being positioned within said housing at a juncture of said first and second portions.

2. The device of claim 1, further including a support member being mounted in said housing and adapted for preventing rotation of said first portion with respect to said second portion.

3. The device of claim 1, further including a light socket being mounted in said first wall, a light bulb being removably positioned in said light socket such that said light bulb extends away from said housing, said light socket being electrically coupled to said moving assembly such that said light bulb is turned on when said moving assembly is actuated by said actuating apparatus.

4. The device of claim 3, further including a sealing ring being attached to and extending along an edge of the upper portion.

5. The device of claim 1, further including a sealing ring being attached to and extending along an edge of the first portion.

6. A remote control scent dispensing device, said device comprising:
- a housing having a first wall, a second wall and a peripheral wall extending between and being attached to said first and second walls, said peripheral wall having a peripheral break therein such that said housing is divided into a first portion and a second portion;
- a moving assembly being mounted in said housing and being adapted for selectively moving said first portion abutting against or positioned away from said second portion, said moving assembly including:
  - a threaded rod being rotatably coupled to and extending upwardly from said second wall;
  - a tube having an inner threaded surface being attached to and extending downwardly from said first wall, said rod extending inwardly of an open bottom end of said tube and being threadably coupled to said tube;
  - a motor being mounted in said second portion, said motor being mechanically coupled to said rod, said motor being adapted for selectively rotating said rod in a first direction to move said first portion away from said second portion or in a second direction to move said first portion toward said second portion;
  - a support member being mounted in said housing and adapted for preventing rotation of said first portion with respect to said second portion;
- an actuator apparatus being adapted for remotely turning on said moving assembly and selectively moving said first portion with respect to said second portion, said actuator apparatus comprising:
  - a control being mounted in said second portion and being electrically coupled to said motor;
  - a receiver for receiving a wireless signal being electrically coupled to said control;
  - a transmitter for sending a wireless signal;
  - a switch assembly being electrically coupled to said transmitter, said switch assembly including at least two switches, wherein depressing a first of said switches causes a first signal to be sent to said control such that said first portion moves away from said second portion, and wherein depressing a second of said switches causes a second signal to be sent to said control such that said first portion moves toward form said second portion;
- a light socket being mounted in said first wall, a light bulb being removably positioned in said light socket such that said light bulb extends away from said housing, said light socket being electrically coupled to said moving assembly such that said light bulb is turned on when said moving assembly is actuated by said actuating apparatus;
- a coupler being attached to said housing for selectively coupling said housing to a tree limb; and
- a scent dispensing member being positioned within said housing at a juncture of said first and second portions.

7. The device of claim 6, further including a sealing ring being attached to and extending along an edge of the first portion.

8. A remote control scent dispensing device, said device comprising:
- a housing having a first wall, a second wall and a peripheral wall extending between and being attached to said first and second walls, said peripheral wall having a peripheral break therein such that said housing is divided into a first portion and a second portion;
- a moving assembly being mounted in said housing and being adapted for selectively moving said first portion abutting against or positioned away from said second portion;
- an actuator apparatus being adapted for remotely turning on said moving assembly and selectively moving said first portion with respect to said second portion;
- a light socket being mounted in said first wall, a light bulb being removably positioned in said light socket such that said light bulb extends away from said housing, said light socket being electrically coupled to said moving assembly such that said light bulb is turned on when said moving assembly is actuated by said actuating apparatus;
- a coupler being attached to said housing for selectively coupling said housing to a tree limb; and
- a scent dispensing member being positioned within said housing at a juncture of said first and second portions.

* * * * *